(12) United States Patent
Kimblad

(10) Patent No.: US 7,011,669 B2
(45) Date of Patent: Mar. 14, 2006

(54) DEVICE AND METHOD FOR TREATMENT OF ATRIOVENTRICULAR REGURGITATION

(75) Inventor: Per Ola Kimblad, Lund (SE)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 10/383,596

(22) Filed: Mar. 10, 2003

(65) Prior Publication Data

US 2003/0153946 A1  Aug. 14, 2003

Related U.S. Application Data

(63) Continuation of application No. 09/670,082, filed on Sep. 26, 2000, now Pat. No. 6,719,767.

(30) Foreign Application Priority Data

Aug. 11, 2000 (SE) .................................. 0002878

(51) Int. Cl.
*A61B 17/08* (2006.01)
(52) U.S. Cl. ...................................... 606/151; 606/142
(58) Field of Classification Search ........ 606/151–153, 606/157, 158, 142, 139, 213, 216, 219, 221, 606/228; 623/2.1, 1.24–126; 128/898
See application file for complete search history.

(56) References Cited

U.S. PATENT DOCUMENTS

| | | | |
|---|---|---|---|
| 3,805,793 A | 4/1974 | Wright | |
| 4,350,160 A | 9/1982 | Kolesov et al. | |
| 5,080,663 A | 1/1992 | Mills et al. | |
| 5,242,456 A | 9/1993 | Nash et al. | |
| 5,267,958 A | 12/1993 | Buckbinder et al. | |
| 5,330,442 A | 7/1994 | Green et al. | |
| 5,374,275 A | 12/1994 | Bradley et al. | |
| 5,403,326 A | 4/1995 | Harrison et al. | |
| 5,443,446 A | 8/1995 | Shturman | |
| 5,458,131 A | 10/1995 | Wilk | |
| 5,474,573 A | 12/1995 | Hatcher | |
| 5,540,704 A | 7/1996 | Gordon et al. | |
| 5,569,274 A | 10/1996 | Rapacki et al. | |
| 5,573,540 A | 11/1996 | Yoon | |
| 5,575,800 A | 11/1996 | Gordon | |
| 5,578,044 A | 11/1996 | Gordon et al. | |
| 5,601,574 A | 2/1997 | Stefanchik et al. | |
| 5,609,598 A | 3/1997 | Laufer et al. | |
| 5,662,664 A | 9/1997 | Gordon et al. | |
| 5,685,867 A | 11/1997 | Twardowski et al. | |
| 5,695,457 A | 12/1997 | St. Goar et al. | |
| 5,700,272 A | 12/1997 | Gordon et al. | |

(Continued)

*Primary Examiner*—(Jackie) Tan-Uyen T. Ho
(74) *Attorney, Agent, or Firm*—David L. Hauser; Richard B. Cates

(57) ABSTRACT

A device and method for treatment of atrioventricular regurgitation comprises a suturing device. The suturing device is configured to be introducible, via blood vessels leading to the heart, to two leaflets of the atrioventricular valve between the atrium and a corresponding ventricle of the heart. The suturing device is configured for binding together the two leaflets along the free edges of the leaflets. A method of using the device includes inserting the suturing device into a catheter, introducing the catheter to the heart and positioning a distal end of the catheter close to two leaflets of an atrioventricular valve, capturing the free edges of the two leaflets with the suturing device in its open state, binding together the two leaflets by transition of the suturing device into its closed state, and retracting the catheter from the heart. As a result, the closing of the valve is improved.

16 Claims, 3 Drawing Sheets

U.S. PATENT DOCUMENTS

| | | |
|---|---|---|
| 5,713,910 A | 2/1998 | Gordon et al. |
| 5,713,911 A | 2/1998 | Racenet et al. |
| 5,716,367 A | 2/1998 | Koike et al. |
| 5,741,277 A | 4/1998 | Gordon et al. |
| 5,741,279 A | 4/1998 | Gordon et al. |
| 5,792,094 A | 8/1998 | Stevens et al. |
| 5,810,847 A | 9/1998 | Laufer et al. |
| 5,836,956 A | 11/1998 | Buelna et al. |
| 5,849,019 A | 12/1998 | Yoon |
| 5,860,992 A | 1/1999 | Daniel et al. |
| 5,885,238 A | 3/1999 | Stevens et al. |
| 5,891,159 A | 4/1999 | Sherman et al. |
| 5,891,160 A | 4/1999 | Williamson et al. |
| 5,924,424 A | 7/1999 | Stevens et al. |
| 5,928,224 A | 7/1999 | Laufer |
| 5,928,250 A | 7/1999 | Koike et al. |
| 5,968,059 A | 10/1999 | Ellis et al. |
| 5,972,020 A | 10/1999 | Carpentier et al. |
| 6,010,531 A | 1/2000 | Donlon et al. |
| 6,015,417 A | 1/2000 | Reynolds, Jr. |
| 6,015,427 A | 1/2000 | Mueller et al. |
| 6,029,671 A | 2/2000 | Stevens et al. |
| 6,047,700 A | 4/2000 | Eggers et al. |
| 6,056,760 A | 5/2000 | Koike et al. |
| 6,080,182 A | 6/2000 | Shaw et al. |
| 6,083,219 A | 7/2000 | Laufer |
| 6,088,889 A | 7/2000 | Luther et al. |
| 6,117,159 A | 9/2000 | Huebsch et al. |
| 6,157,852 A | 12/2000 | Selmon et al. |
| 6,162,233 A | 12/2000 | Williamson et al. |
| 6,165,183 A | 12/2000 | Kuehn et al. |
| 6,165,204 A | 12/2000 | Levinson et al. |
| 6,190,357 B1 | 2/2001 | Ferrari et al. |
| 6,210,419 B1 | 4/2001 | Mayenberger et al. |
| 6,234,995 B1 | 5/2001 | Peacock |
| 6,312,447 B1 * | 11/2001 | Grimes ........................ 606/219 |
| 6,443,922 B1 | 9/2002 | Roberts et al. |
| 6,508,777 B1 | 1/2003 | Macoviak et al. |
| 6,582,388 B1 | 6/2003 | Coleman et al. |
| 2002/0049402 A1 | 4/2002 | Peacock et al. |

* cited by examiner

DEVICE AND METHOD FOR TREATMENT OF ATRIOVENTRICULAR REGURGITATION

This is a continuation of parent application Ser. No. 09/670,082 filed Sep. 26, 2000, now U.S. Pat. No. 6,719,767.

BACKGROUND OF THE INVENTION

The invention relates to a device for treatment of atrioventricular regurgitation and a method for treatment of atrioventricular regurgitation using said device.

The heart has two atrioventricular valves, the mitral valve, which is situated between the left atrium and the left ventricle, and the tricuspid valve situated between the right atrium and the right ventricle. The tricuspid valve has three leaflets, two of which are much bigger than the third. These two bigger leaflets could be considered to correspond to the two leaflets of the mitral valve. Therefore, only the mitral valve will hereinafter be discussed although corresponding discussions could apply to the tricuspid valve.

Mitral regurgitation is the medical name of a problem that occurs in the heart. A person that suffers from mitral regurgitation has a mitral insufficiency, i.e. the mitral valve between the left atrium and the left ventricle cannot close entirely. Thus, when the ventricle is contracted in order to pump out blood through the aorta, some blood leaks back into the atrium instead. This will lead to a reduced functionality of the left ventricle and subsequently to heart insufficiency, which is a mortal disease.

Mitral insufficiency can result from, for example, ischemic disease, degenerative disease of the mitral apparatus, rheumatic fever, endocarditis, congenital heart disease and cardiomyopathy. The four major structural components of the mitral valve are the annulus, the two leaflets, the chordae and the papillary muscles. Any one or all of these in different combinations may be injured and create insufficiency.

At present mitral regurgitation is treated by open-heart surgery. This is a major operation and requires the use of total cardiopulmonary by-pass, aortic cross clamping and cardioplegic arrest. To certain groups of patients this is particularly hazardous and there is an apparent risk of not surviving the operation.

The treatment consists of either mitral valve replacement or repair. Replacement can be performed with either mechanical or biological valves.

The mechanical valve carries the risk of thromboembolism and requires anticoagulation, with all its potential hazards, whereas biological prostheses suffer from limited durability. Another hazard in connection with replacement is the risk of endocarditis. These risks and other valve related complications are greatly diminished with valve repair.

The four basic techniques of repair include the use of an annuloplasty ring, quadrangular segmental resection of diseased posterior leaflet, shortening of elongated chordae, and transposition of posterior leaflet chordae to the anterior leaflet. The techniques of mitral valve repair rely on decreasing valve area to increase leaflet apposition, but fail to address subvalvular dysfunction. Mitral insufficiency caused by prolapse of the anterior leaflet, posterior leaflet with calcified annulus, or prolapse of both leaflets constitutes a more demanding challenge to repair.

In 1995 Alfieri et al introduced modifications in the operative technique that allow a more expeditious and reproducible procedure than the traditional of greater complexity. This is achieved by simply anchoring the prolapsing free edge of the leaflet to the facing edge of the other leaflet (edge-to-edge technique), thus creating a double orifice of the mitral valve. The hemodynamic behavior of a double orifice mitral valve does not differ from that of a physiological valve of the same total area. Pressure drops and flow velocity across the valve are not influenced by the configuration of the valve.

Some efficient methods of treating mitral insufficiency exist as shown above, but all of them require open-heart surgery. Since many patients with mitral regurgitation are elderly or have a poor left ventricular function, they would benefit from a less invasive procedure that does not involve the use of cardiopulmonary by-pass as required by conventional techniques.

SUMMARY OF THE INVENTION

The object of the invention is to provide a device and a method for treatment of atrioventricular regurgitation that will be applicable to a beating heart.

Thus, a device for treatment of atrioventricular regurgitation comprises a suturing means having such dimensions as to be introducible, via blood vessels leading to the heart, to two leaflets of an atrioventricular valve between an atrium and a corresponding ventricle of the heart and being designed for binding together the two leaflets in a position along the free edges of the leaflets, whereby the closing of the atrioventricular valve is improved.

Preferably, the atrioventricular valve is the mitral valve between the left atrium and the left ventricle of the heart.

Diseases to the atrioventricular valves are much more common in the mitral valve than in the tricuspid valve. Therefore the focus of the invention is on the treatment of the mitral valve although treatment of the tricuspid valve could work equally well using the device.

The suturing means is preferably transitional between two states, being open in a first state and substantially closed in a second state.

This makes the suturing means capable of reaching the free edges of the mitral leaflets in the first state and of bringing them closer to each other when transitioned into the second state.

In a preferred embodiment, the suturing means comprises a clip.

Preferably, the clip has two arms pivotally connected to each other at a first end thereof, the arms forming a V in the first state of the clip and being substantially parallel in the second state of the clip.

Consequently, the arms of the clip can capture both mitral leaflets in the first state and bring them closer together in the second state.

Desirably, the arms of the clip have second, free ends bent towards each other so that these ends of the arms in the second state of the clip are brought proximal to each other.

This means that the mitral leaflets can be brought in close proximity to create a suture as the ends of the arms capturing the mitral leaflets in the second state of the clip are brought proximal to each other.

Further, each second end of the arms is preferably sharp.

As a result, the clip can easily capture the mitral leaflets and are capable of gripping the leaflets between its arms.

Suitably, the clip has two pairs of arms connected to each other by two crossbars near the connected first ends of the arms.

This means that the clip can get a good and lasting grip on the mitral leaflets.

Preferably, the device comprises a catheter for introduction of the clip via the blood vessels into the heart, said catheter having an outermost sheet covering the clip and being retractable therefrom.

This allows the clip to easily be introduced into the heart and there be uncovered for application to the mitral valve.

In one embodiment the catheter has a rod for holding the clip substantially in the open state within the outermost sheet and an applicator for pushing the clip off the rod for transition thereof into the closed state when the outermost sheet is retracted from the clip.

This is desirable for the application of the suturing means, as the transition between the two states of the suturing means can be controlled for capturing and suturing of the mitral leaflets.

In another embodiment the catheter has a rod for holding the clip substantially in the open state within the outermost sheet, said rod also having a puncturing means at a distal tip thereof.

This means that the catheter can be introduced via a vein since the puncturing means can be used to puncture the interatrial septum so as to enable the device to be brought into the left atrium from the right atrium.

Preferably, the suturing means consists of a memory material such as Nitinol.

As a result, the suturing means can easily be made to transform from its first state to its second and thereafter maintain its second state.

According to the present invention, the method for treatment of atrioventricular regurgitation comprises the steps of providing a suturing means having an open state and a closed state; inserting the suturing means into the distal end of a catheter; introducing the catheter via blood vessels leading to the heart, so as to position the distal end of the catheter close to the free edges of two leaflets of an atrioventricular valve between an atrium and a corresponding ventricle of the heart; capturing the free edges of the two leaflets with the suturing means in its open state; binding together the two leaflets by transition of the suturing means into its closed state; and retracting the catheter from the heart while leaving the suturing means fixed on the two leaflets.

Preferably, the atrioventricular valve is the mitral valve between the left atrium and the left ventricle.

Preferably, the suturing means is covered with a protective sheet of the catheter when introduced into the distal end thereof and uncovered by retraction of the protective sheet when positioned close to the free edges of the two leaflets of the atrioventricular valve.

Consequently, the suturing means can be introduced into the heart in a convenient way and be exposed in the ventricle.

In a mitral valve embodiment of the invention the catheter is introduced into the brachial or femoral artery and is passed retrograde to the blood flow through the aorta to the left ventricle.

In another mitral valve embodiment the catheter is introduced into a vein and passed up to the heart via the vein. The catheter could be introduced through any suitable vein, such as the femoral, jugular or subclavian veins. In this embodiment, the catheter preferably has a puncturing means on a distal tip thereof, such that the interatrial septum may be punctured by said puncturing means and the catheter be introduced through the septum to the left atrium and then passed to the left ventricle.

This means that the catheter may be introduced through the femoral vein since a passage from the right side of the heart to the left side is achievable.

BRIEF DESCRIPTION OF THE DRAWINGS

The invention will be better understood by means of the following description of preferred embodiments referring to the accompanying drawings, in which.

DESCRIPTION OF THE PREFERRED EMBODIMENTS

The device will now be described with reference to its use on a mitral valve. However, it is obvious that the device could also be used on the two biggest leaflets of the tricuspid valve.

Figure 1:
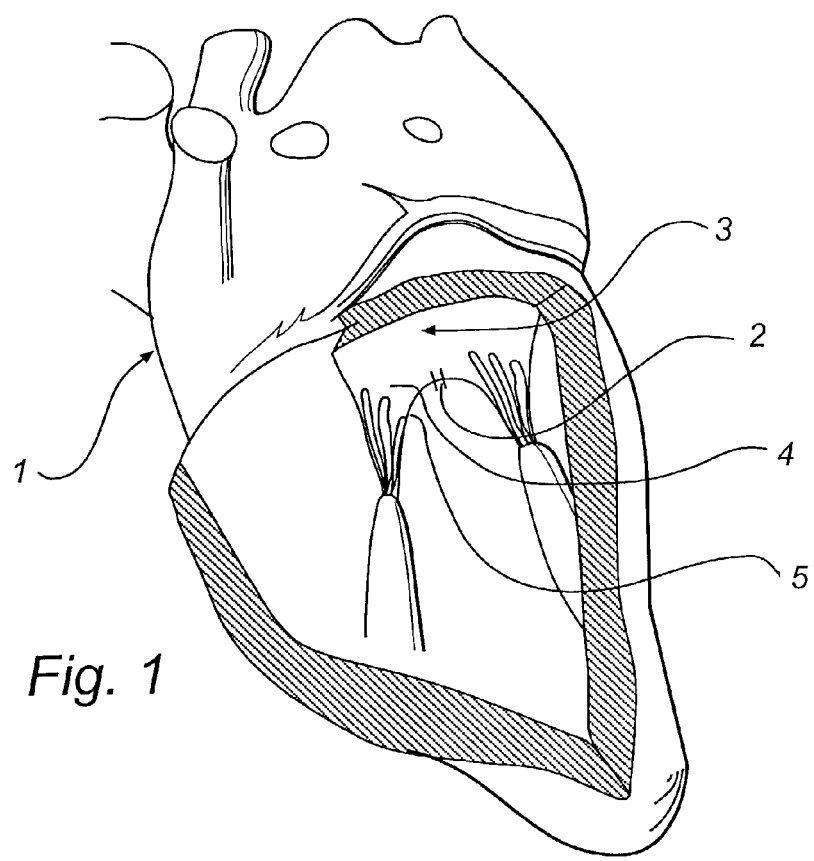
FIG. 1 is a partially sectional view of a heart having a suturing means applied on the mitral valve according to the present invention.

FIG. 1 shows a heart 1. The left side of the heart 1 is shown in section. A clip constituting a suturing means 2 is applied to the free edges of the mitral valve 3 keeping the mitral leaflets 4, 5 together in a connection point so as to create a double orifice, one orifice on each side of the connection point, thus allowing the leaflets 4, 5 to close completely.

In the following there will be described a device and a method for creating a double orifice in the mitral valve 3 of a beating heart 1.

Figure 2:
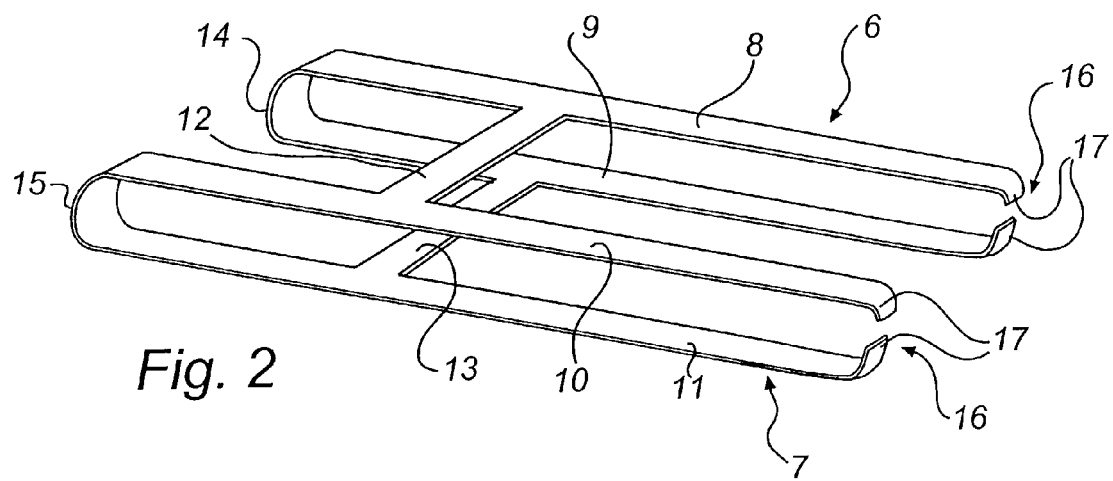
FIG. 2 is a perspective view of a suturing means according to the present invention.

Referring now to FIG. 2, an enlargement of the suturing means 2 is showed. The suturing means 2 being a clip consists of two pairs 6, 7 of arms 8–9 and 10–11. The arms 8–9 and 10–11 in the pairs are connected in one end 14, 15 and thus are formed in one piece. In their other end the arms 8–9 and 10–11 are bent towards each other in a bent portion 16. The bent portions 16 are terminated with a sharp tip 17 so as to be able to engage and grab the mitral leaflets 4, 5.

The clip 2 has two parallel crossbars 12, 13 that each connect one arm 8, 9 in one pair 6 to one arm 10, 11 in the other pair 7. The crossbars 12, 13 are equally long and are connected to the arms 8–9 and 10–11 at equal distance from the connections 14, 15. The pairs 6, 7 of arms are thus kept parallel by the crossbars 12, 13. The crossbars 12, 13 are attached to the arms 8–9 and 10–11 near the connection ends 14, 15.

The clip 2 is made of a memory metal, such as Nitinol, and in FIG. 2 it is shown in a second state where the arms 8–9 and 10–11 in the pairs are parallel and the bent portions 16 in their ends are brought in close proximity to each other. The memory material of the clip 2 biases the clip 2 towards its second, closed state. In a first state, the arms 8–9 and 10–11 in the pairs are opened, forming a V, as the angle in their connections 14, 15 is increased. The clip 2 is capable of grasping the mitral leaflets 4, 5 at their free edges and bind the edges together by capturing the leaflets 4, 5 in the first state of the clip 2 and keeping them together in the second state of the clip 2, where the arms are closed and parallel.

Figure 3:
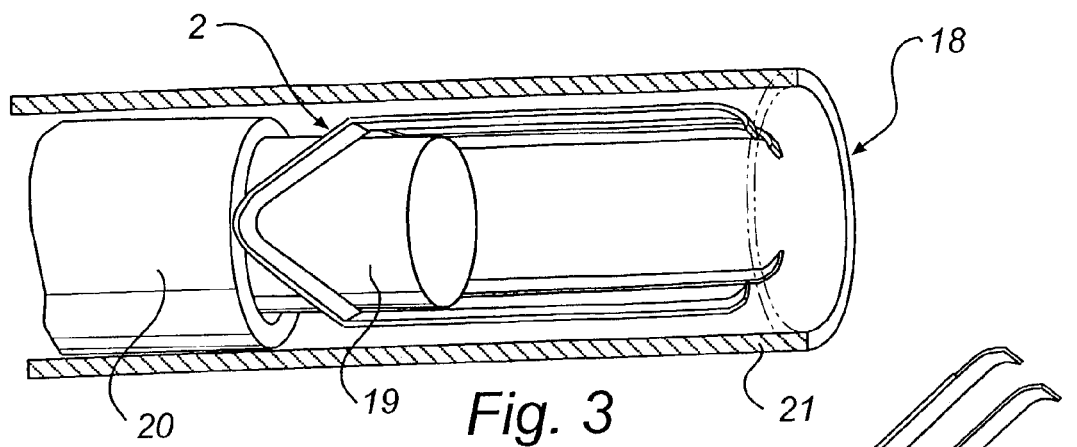
FIG. 3 is a sectional view of a catheter carrying a suturing means according to one embodiment of the invention.
Figure 4:
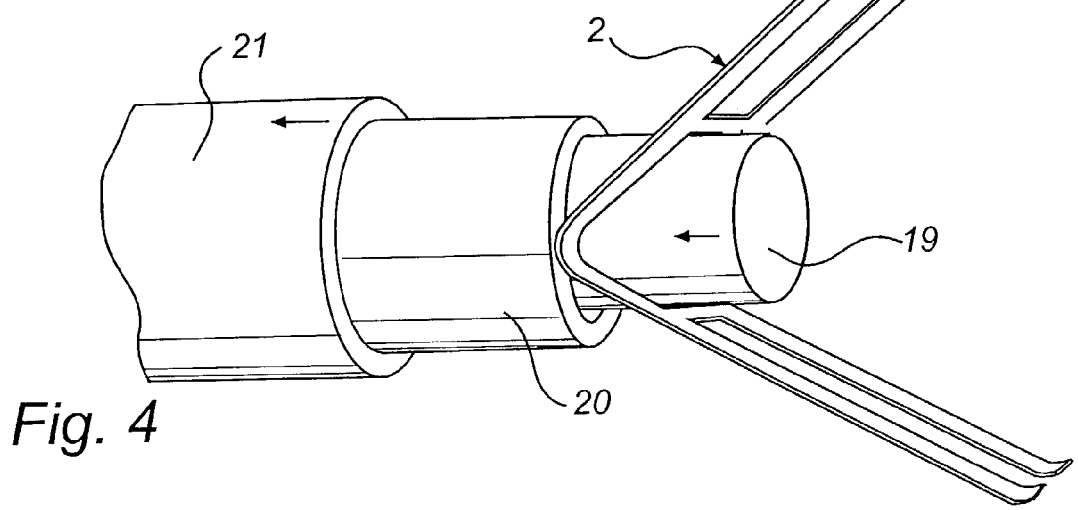
FIG. 4 is a perspective view of the catheter in FIG. 3 carrying a suturing means that has been unsheathed.

The clip 2 is inserted into a beating heart 1 by using a catheter. Referring to FIGS. 3 and 4, a first embodiment of a catheter 18 will be described. In its innermost part the catheter 18 has a supportive rod 19 that is slidable in a hollow applicator 20. In its outermost part the catheter 18 has a protective sheet 21 that also is slidable upon the applicator 20.

The clip 2 is attached in a distal end of the catheter to the applicator 20. The attachment is made in the connections 14, 15 of the arms 8–9 and 10–11 in the pairs. The supportive rod 19 can be extended out of the applicator 20 and be held between the two crossbars 12, 13 of the clip 2. The supportive rod 19 does in this condition hold the arms 8–9 and 10–11 in the pairs of the clip 2 apart, keeping the clip 2 in its first, open state. The protective sheet 21 can be pushed over the clip 2 to make the catheter 18 easier to introduce into the heart 1 and keep the arms 8–9 and 10–11 in the pairs parallel from the crossbars 12, 13 towards the bent portions 16 as shown in FIG. 3, the clip 2 still being held substantially in the open state. In this way the clip 2 does not get stuck as it is passed into the heart 1.

In FIG. 4 the protective sheet 21 is drawn back along the applicator 20, thus uncovering the clip 2 and allowing the clip 2 to take the form of its first state. The clip 2 can then be transformed into its second state by retracting the supportive rod 19 that keeps the crossbars 12, 13 of the clip 2 apart.

Figure 6:
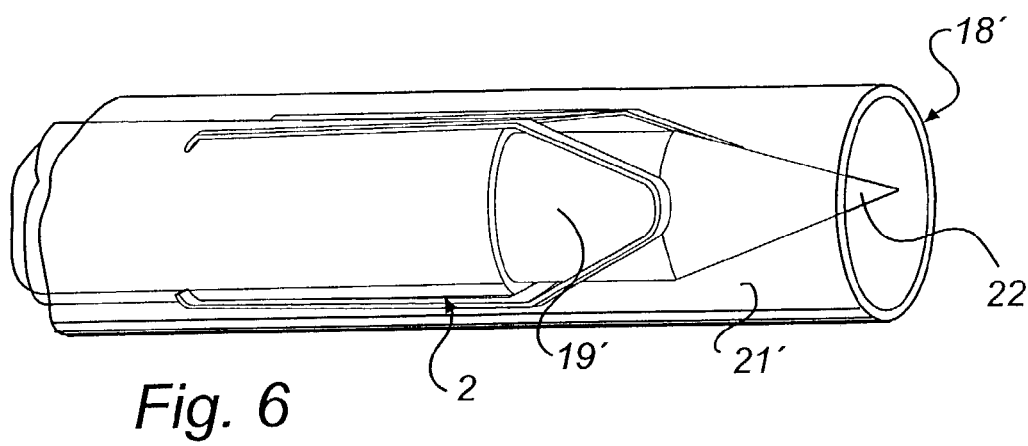
FIG. 6 is a sectional view of a catheter carrying a suturing means according to another embodiment of the present invention.
Figure 7:
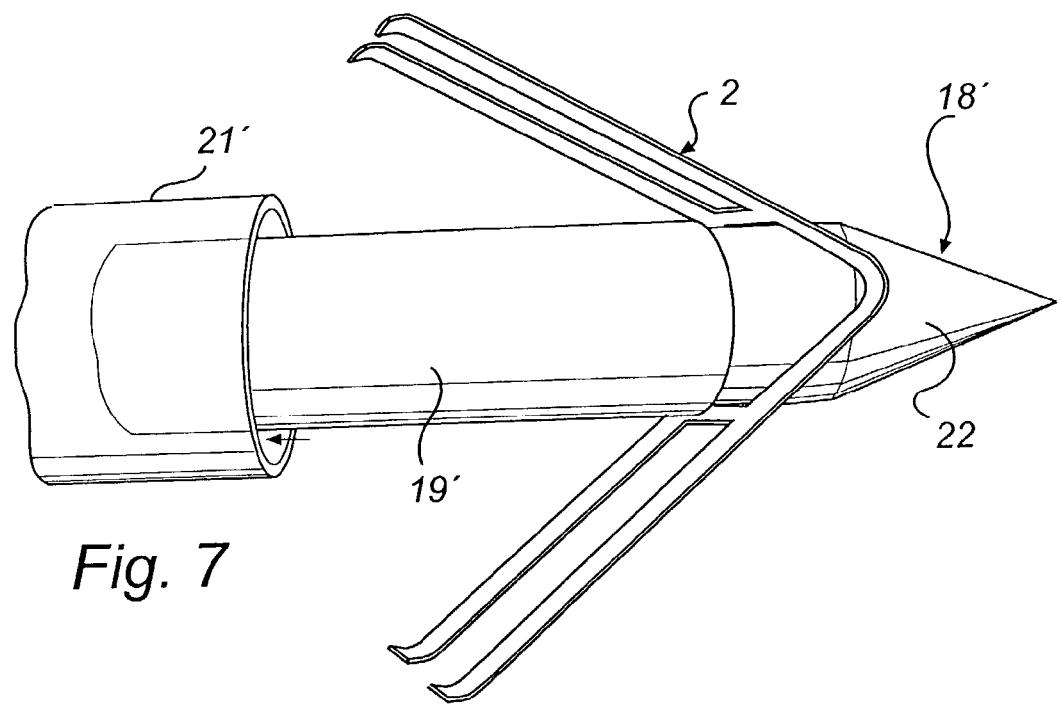
FIG. 7 is a perspective view of the catheter in FIG. 6 carrying a suturing means that has been unsheathed according to another embodiment of the invention.

A second alternative embodiment of the catheter 18' is shown in FIGS. 6 and 7. The catheter 18' comprises a supportive rod 19' that in the distal end of the catheter can be entered and held between the two crossbars 12, 13 of the clip 2 and extend past the connection ends 14, 15 of the arms 8–9 and 10–11 in the pairs. The supportive rod 19' does in this condition hold the arms 8–9 and 10–11 in the pairs of the clip 2 apart, thus keeping the clip 2 in its first state.

In its distal end the supportive rod 19' has a needle 22 that can be used to puncture the interatrial septum. The catheter 18' has an outermost protective sheet 21' that is slidable upon the supportive rod 19'. When the catheter 18' is inserted into the heart 1, the protective sheet 21' covers the clip 2 keeping the arms 8–9 and 10–11 in the pairs parallel from the crossbars 12, 13 towards the bent portions 16 as shown in FIG. 6 and also covers the needle 22 of the supportive rod 19'. However, the clip 2 is still held substantially in the open state with its free ends 16 apart. As the protective sheet 21' is drawn back, it first uncovers the needle 22 allowing it to puncture the interatrial septum and then uncovers the clip 2 allowing it to take the form of its first state. The supportive rod 19' can then be retracted making the clip 2 transform into its second state.

The catheter 18, 18' could also have an ultrasound probe to provide an easy way for visualizing the device inside the heart 1. The supportive rod 19, 19' could be designed to also provide the ultrasound probe. Ultrasound could also be used in other ways for visualization, e.g. by inserting an ultrasound probe inside the oesophagus.

Two alternative methods for inserting the device for treating mitral regurgitation will be described in the following. The insertion is done into a beating heart and can be performed in local anesthesia.

Both methods include an introduction of a catheter into the heart. These introductions described below are standard techniques currently used for diagnostic left heart catheterization.

Figure 5:
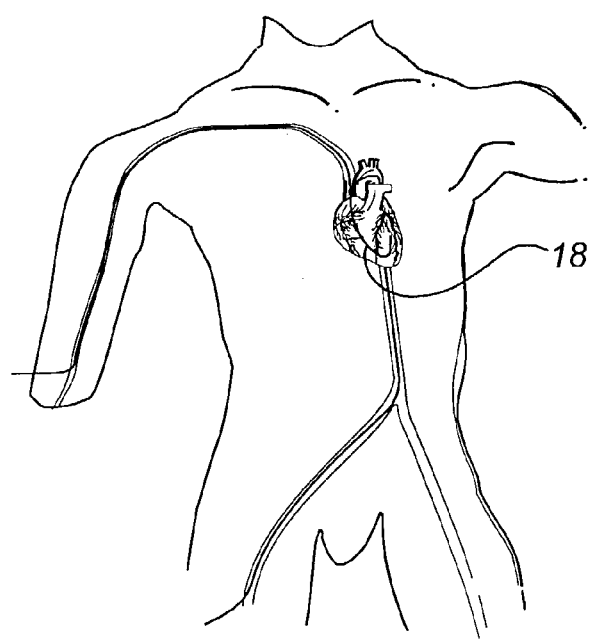
FIG. 5 shows schematically how a device according to the invention can be inserted through an artery into the left ventricle of the heart.

The first method uses the catheter 18 shown in FIGS. 3 and 4. Referring to FIG. 5, the catheter 18 is inserted into the body through the brachial or the femoral artery. The catheter 18 is then passed retrograde along the artery into the left ventricle of the heart 1. The protective sheet 21 is then retracted as shown in FIG. 4, thus uncovering the clip 2. The clip 2 is now in its first, open state and is used to capture the mitral leaflets 4, 5, preferably in the middle of their free edges. The sharp ends 17 of the bent portions 16 of the arms 8–11 give a steady grip on the mitral leaflets 4, 5. The supportive rod 19 is then retracted, thus allowing the clip 2 to transform into its second state. The clip 2 thereby closes and keeps the captured parts of the two mitral leaflets 4, 5 together. The clip 2 is now in place to grasp and approximate the free edges of the mitral leaflets 4, 5 by the edge-to-edge technique. A double orifice, one on each side of the suture, is thus formed. This double orifice can be closed completely by the mitral valve. Finally, the catheter 18 is retracted from the heart 1, leaving the clip 2 forming the double orifice.

Figure 8:
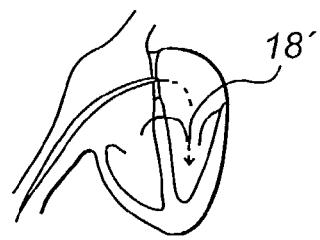
FIG. 8 shows schematically how a device according to the invention can be inserted through a vein into the left ventricle of the heart.

The second method uses the catheter 18' shown in FIGS. 6 and 7. The catheter 18' is inserted into the body through the femoral vein. The catheter 18' could be inserted through any other suitable vein, such as the jugular or the subclavian vein. Referring to FIG. 8, the catheter 18' is passed along the femoral vein into the vena cava and further into the right atrium. The needle 22 in the distal end of the supportive rod 19' is unsheathed by a retraction of the protective sheet 21' of the catheter 18'. The needle 22 is then used to puncture the interatrial septum to give the catheter 18' a passage into the left atrium and then through the mitral valve into the left ventricle. When the catheter has been passed into the left ventricle, the protective sheet 21' is retracted further, whereupon the clip 2 unfolds. The clip 2 is now in its first, open state and the mitral leaflets 4, 5 can be captured in the same manner as described for the first method. When the supportive rod 19' is retracted, the clip 2 transforms into its second state, thus closing and keeping the mitral leaflets 4, 5 together. The clip 2 is now in place to grasp and approximate the free edges of the mitral leaflets 4, 5 by the edge-to-edge technique. As for the first method a double orifice that the mitral valve can close completely is created. Finally the catheter 18' is retracted completely from the body leaving the clip 2 forming the double orifice.

When treating tricuspid regurgitation the catheter 18' is used without the needle 22 on the distal end of the supportive rod 19'. The catheter 18' is inserted into the body through a vein, such as the femoral, jugular or subclavian veins. The catheter 18' is passed along the vein into the right atrium of the heart 1. The catheter 18' is then inserted through the tricuspid valve into the right ventricle. Here the protective sheet 21' is retracted to uncover the clip 2 and the capture of the two biggest leaflets of the tricuspid valve could be performed in the same manner as described for the mitral valve described above. Finally, the catheter 18' is retracted leaving the device fixed on two leaflets of the tricuspid valve.

Although particular embodiments of the present invention have been described, the application is not limited to these embodiments but includes modifications that are obvious to the skilled man and are comprised in the scope of the invention as defined in the appended claims. For example, it is obvious that different embodiments of clips can be designed. Modifications of the suturing means are possible in numerous ways without extending beyond the spirit of the invention.

What is claimed is:

1. A method of stabilizing a first heart valve leaflet in a heart, comprising:
   providing a delivery catheter;
   providing a clip formed from a temperature-activated memory material;
   securing the clip in a delivery state to the delivery catheter;
   advancing the clip to a desired position adjacent the first heart valve leaflet;
   transforming the clip from the delivery state to an open state, wherein the clip is in an open position with a clip opening configured to receive an edge of the first heart valve leaflet;
   positioning an edge of the first heart valve leaflet within the clip opening; and
   transforming the clip from the open state to a closed state, whereby the edge of the first heart valve leaflet is secured within the clip.

2. The method of claim 1, wherein the memory metal of the clip biases the clip toward the closed state.

3. The method of claim 2, wherein securing the clip in the delivery state to the delivery catheter comprises mechanically biasing the clip toward the open state and mechanically holding the clip in the delivery state.

4. The method of claim 3, wherein transforming the clip to the open state comprises releasing the mechanical holding of the clip in the delivery state.

5. The method of claim 1, further comprising:
   prior to transforming the clip to the closed state, positioning an edge of a second heart valve leaflet within the clip opening, whereby when the clip is transformed to the closed state the edge of the second heart valve leaflet is secured within the clip.

6. An apparatus for securing a first heart valve leaflet, the apparatus comprising:
   a clip comprising a first end and a second end, the clip having an open state, a delivery state, and a closed state, the clip comprising a memory metal and being biased toward the closed state; and
   a delivery catheter, the delivery catheter comprising a first member configured to mechanically bias the clip toward the open state, and a second member configured to mechanically bias the clip toward the delivery state.

7. The apparatus of claim 6, wherein the delivery catheter has a distal end and further comprises a needle at the distal end, the needle configured to puncture an interatrial septum of a patient's heart.

8. The apparatus of claim 6, wherein the delivery catheter first member comprises a supportive rod configured to engage the first end of the clip.

9. The apparatus of claim 8, wherein the supportive rod comprises a distal end having a needle thereon, the needle configured to puncture an interatrial septum of a patient's heart.

10. The apparatus of claim 9, wherein the delivery catheter comprises a generally tubular outer member, and the supportive rod is slideable within the generally tubular outer member.

11. The apparatus of claim 6, wherein the delivery catheter second member comprises a generally tubular member configured to slideably receive the clip, thereby engaging the second end of the clip and mechanically biasing the clip toward the delivery state.

12. A method of stabilizing a first heart valve leaflet in a heart, comprising:
   providing a delivery catheter;
   providing a clip formed from a memory material;
   securing the clip in a delivery state to the delivery catheter;
   advancing the clip to a desired position adjacent the first heart valve leaflet, wherein advancing the clip comprises advancing the clip into the right atrium of the heart, puncturing the interatrial septum of the heart, and advancing the clip through the interatrial septum and into the left atrium of the heart;
   transforming the clip from the delivery state to an open state, wherein the clip is in an open position with a clip opening configured to receive an edge of the first heart valve leaflet;
   positioning an edge of the first heart valve leaflet within the clip opening; and
   transforming the clip from the open state to a closed state, whereby the edge of the first heart valve leaflet is secured within the clip.

13. The method of claim 12, wherein the memory metal of the clip biases the clip toward the closed state.

14. The method of claim 13, wherein securing the clip in the delivery state to the delivery catheter comprises mechanically biasing the clip toward the open state and mechanically holding the clip in the delivery state.

15. The method of claim 14, wherein transforming the clip to the open state comprises releasing the mechanical holding of the clip in the delivery state.

16. The method of claim 12, further comprising:
   prior to transforming the clip to the closed state, positioning an edge of a second heart valve leaflet within the clip opening, whereby when the clip is transformed to the closed state the edge of the second heart valve leaflet is secured within the clip.

* * * * *